United States Patent [19]

Baldwin et al.

[11] 4,205,075
[45] May 27, 1980

[54] PROCESSES AND COMPOSITION FOR COMBATING FUNGI

[75] Inventors: Brian C. Baldwin, Wargrave;
Margaret C. Shephard, Maidenhead;
Anthony M. Skidmore, Wokingham,
all of England

[73] Assignee: Imperial Chemical Industries Limited, London, England

[21] Appl. No.: 820,630

[22] Filed: Jul. 29, 1977

[30] Foreign Application Priority Data

Jul. 29, 1976 [GB] United Kingdom ............... 31649/76

[51] Int. Cl.² .................. A01N 9/02; A01N 9/22; A01N 9/28
[52] U.S. Cl. ........................... 424/269; 71/81; 424/279
[58] Field of Search .............. 424/269, 279; 71/89

[56] References Cited

FOREIGN PATENT DOCUMENTS

| | | |
|---|---|---|
| 844909 | 2/1977 | Belgium . |
| 1433576 | 4/1966 | France . |
| 48-01493 | 1/1973 | Japan . |
| 754111 | 5/1975 | South Africa . |
| 914893 | 1/1963 | United Kingdom . |
| 1491856 | 11/1977 | United Kingdom . |

OTHER PUBLICATIONS

Lang; Ann. Review Plant Physiol, 21 (1970) pp. 537–570.
Buchenauer et al; "Triadimefon" Int. Therapy of Plants 8/22–28/76.
Leopold; Plant Physiol, (1971) 48 pp. 537–540.
Sisler et al, Internal Therapy of Plants 8/22–28/76 1976.
Shive et al; Plant Physiol, (1976) 57, pp. 640–644.
Palevitch et al; Physio Plant 37, 247–252 (1976).
Coolbaugh et al; Plant Physiol, (1976) 57, pp. 245–248.

*Primary Examiner*—Allen J. Robinson
*Attorney, Agent, or Firm*—Cushman, Darby & Cushman

[57] ABSTRACT

Anti-fungal compositions for combating plant and seed fungi comprise (a) a triazole derivative of formula:

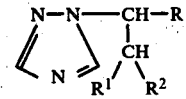

or a salt, or isomer, or metal complex thereof where R is —COX, —CH(OH)X, or —C($R^3$) (OH)X where X is iso-propyl or tertiary-butyl or phenyl optionally substituted with halogen and $R^3$ is $C_1$ to $C_4$ alkyl; $R^1$ is H, OH or $C_1$ to $C_4$ alkyl; $R^2$ is phenyl optionally substituted with halogen, $NO_2$ or halo-alkyl; and (b) gibberellic acid, or other gibberellin.

2 Claims, No Drawings

PROCESSES AND COMPOSITION FOR COMBATING FUNGI

This invention relates to anti-fungal compositions and to processes for combating fungi; more particularly the invention relates to compositions for, and processes of, treating plants and seeds.

There has long existed a need to protect plants and seeds from the adverse effects upon them of foliage-, seed- and soil-borne fungal diseases. Fungi infecting seed may often cause it to fail to germinate, or to give rise to diseased seedling plants, the ability of which to survive is considerably diminished as a result. Plants infected by fungi often fail to yield a good crop upon harvesting.

To alleviate these adverse affects, plants and seeds have, for many years, been treated with chemical substances which have anti-fungal activity and therefore combat the fungal disease.

Many such chemical substances, however, have limitations upon the extent to which they can be used, and one particular restriction is the tendency of some of them to give rise to undesirable side-effects upon the plants counterbalancing, at least to some extent, the beneficial effects stemming from a combating of the fungal disease.

The undesirable side-effects include the following:
(a) Hindrance of seed germination.
(b) Stunting of the growth of the plants.
(c) Phytotoxic effects of varying degree.

We have now found a way in which these undesirable effects can be reduced for certain specified chemical substances, as hereinafter described, which are otherwise excellent fungicides, so that they may be more safely deployed with respect to any adverse effects upon plants and seeds and without diminishment of their fungicidal activity.

The invention provides a composition for combating fungi comprising (a) an anti-fungal chemical substance and having the formula:

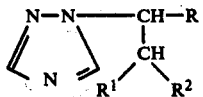

or salt, or isomer, or metal complex thereof, wherein R is a group —COX, —CH(OH)X or —C(R$^3$)(OH)X where X is iso-propyl or tertiary-butyl or phenyl optionally substituted with one or more halogen atoms and R$^3$ is a lower alkyl group having up to 4 carbon atoms, R$^1$ is hydrogen, hydroxyl, or alkyl having up to 4 carbon atoms, R$^2$ is phenyl optionally substituted with one or more halogen atoms or nitro- or haloalkyl-groups; and (b) gibberellic acid, or other gibberellin.

Preferred haloalkyl groups are trifluoromethyl groups.

R is preferably the group —CH(OH)C(CH$_3$)$_3$. R$^1$ is preferably hydrogen or methyl, especially hydrogen. R$^3$ when not hydrogen is preferably methyl. R$^2$ is preferably phenyl substituted with one or two chlorine or fluorine atoms, especially chlorine atoms; more specifically R$^2$ is preferably 4-chlorophenyl, 2-chlorophenyl or 2,4-dichlorophenyl.

Preferred compositions according to the invention are those wherein the anti-fungal chemical substance corresponds to the general formula shown above but has the preferred substitution as set out in the preceding paragraph.

Particularly preferred compositions contain any of the specific substances listed, by way of exemplification only, in Table I hereinbelow, especially compound No. 1 thereof.

TABLE I

| COMPOUND NO | STRUCTURAL FORMULA |
| --- | --- |
| 1 | 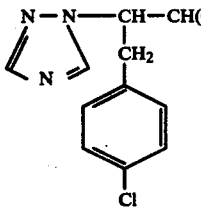<br>Isomer A |
| 2 | 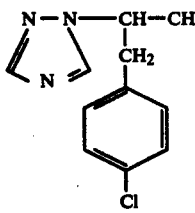<br>Isomer B<br>(Isomer of Compound No. 1) |
| 3 | 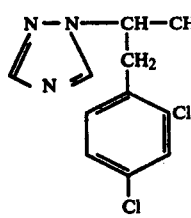 |
| 4 | 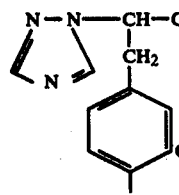 |
| 5 | 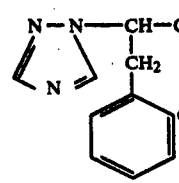 |
| 6 | 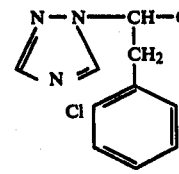 |

TABLE I-continued

| COMPOUND NO | STRUCTURAL FORMULA |
|---|---|
| 7 | 1-(2-chlorobenzyl)-2-(1,2,4-triazol-1-yl)-1-(2,2-dimethyl-1-hydroxypropyl), with 2-Cl and F on phenyl |
| 8 | triazolyl-CH(CH(OH)C(CH$_3$)$_3$)-CH$_2$-phenyl(2-Cl) |
| 9 | triazolyl-CH(CH(OH)C(CH$_3$)$_3$)-CH$_2$-phenyl(4-F) |
| 10 | triazolyl-CH(CH(OH)C(CH$_3$)$_3$)-CH$_2$-phenyl |
| 11 | triazolyl-CH(CH(OH)C(CH$_3$)$_3$)-CH$_2$-phenyl(2-F) |
| 12 | triazolyl-CH(CH(OH)C(CH$_3$)$_3$)-CH$_2$-phenyl(3-F) |
| 13 | triazolyl-CH(CH(OH)C(CH$_3$)$_3$)-CH$_2$-phenyl(2,4-F$_2$) |
| 14 | triazolyl-CH(CH(OH)C(CH$_3$)$_3$)-CH$_2$-phenyl(3-Br) |
| 15 | triazolyl-CH(CH(OH)C(CH$_3$)$_3$)-CH$_2$-phenyl(4-Br) |
| 16 | triazolyl-CH(CH(OH)C(CH$_3$)$_3$)-CH$_2$-phenyl(4-NO$_2$) |
| 17 | triazolyl-CH(CH(OH)C(CH$_3$)$_3$)-CH$_2$-phenyl(3-CF$_3$) |
| 18 | triazolyl-CH(CH(OH)C(CH$_3$)$_3$)-CH$_2$-pyridyl(Cl, NO$_2$) |
| 19 | triazolyl-CH(C(CH$_3$)(OH)C(CH$_3$)$_3$)-CH$_2$-phenyl(F) |
| 20 | triazolyl-CH(CH(OH)·C(CH$_3$)$_3$ with CH$_3$)-CH$_2$-phenyl(Cl) |
| 21 | triazolyl-CH(CH(OH)CH(CH$_3$)$_2$)-CH$_2$-phenyl(Cl) |

TABLE I-continued

| COMPOUND NO | STRUCTURAL FORMULA |
|---|---|
| 22 | 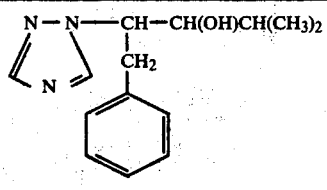 |
| 23 | 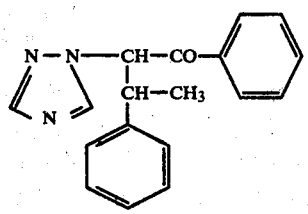 |
| 24 | 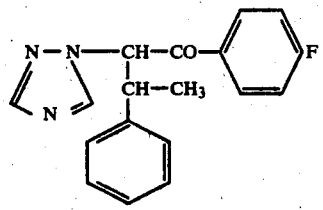 |
| 25 | 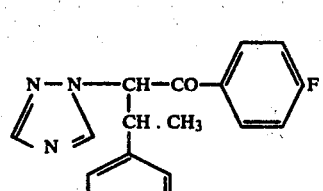 |
| 26 | 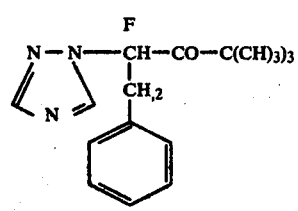 |

These substances, their preparation, and their deployment as, for example, fungicides and for plant growth regulation, are described and claimed in copending British patent applications Nos. 31650/76, 34590/76, 42667/76 and 5139/77.

Thus the compounds of the general formula:

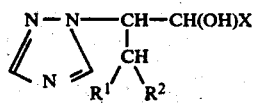

or a salt thereof, can be prepared by reducing a compound of general formula (II):

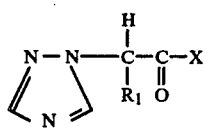

wherein $R_1$ is optionally substituted benzyl and X is as defined above, or a salt thereof. Suitable reducing agents are sodium borohydride or lithium aluminium hydride. If desired, catalytic hydrogenation using a suitable metal catalyst can be used. When the compound of general formula (II) is a sterically hindered ketone, a Grignard reagent, for example butylmagnesium halide (e.g. bromide or iodide) can be used as the reducing agent.

The reduction can be performed by dissolving the reactants in a solvent such as diethyl ether or tetrahydrofuran (for lithium aluminium hydride reduction) or water (for sodium borohydride reduction). The reaction temperature will depend on the reactants and solvent; but generally the reaction mixture is heated under reflux. After the reaction, the product can be isolated by extraction into a convenient solvent after acidification with dilute mineral acid. On removal of the solvent in vacuo, the product may be crystallised from a convenient solvent.

The compounds of general formula (I) wherein $R_3$ is alkyl, or a salt thereof, can be prepared by reacting a compound of general formula (II) or a salt thereof with the appropriate Grignard reagent e.g. an alkyl magnesium halide such as methyl magnesium bromide or iodide. This reaction can be performed by methods known in the art.

The starting compound of general formula (II) may be made by reacting 1,2,4-triazole, or a salt thereof, with a α-haloketone of general formula (III):

wherein X is halogen, preferably bromine or chlorine, and $R_1$ and $R_2$ are as defined above. This process may be carried out by heating the reactants together in the absence of a solvent or diluent, but preferably a solvent is present.

Suitable solvents are non-hydroxylic solvents such as acetonitrile, dimethylformamide, dimethyl sulfoxide, sulpholane and tetrahydrofuran. Hydroxylated solvents, for example, methanol and ethanol, may be used in certain circumstances when the presence of the hydroxyl group does not interfere with the reaction. The process can be carried out in the presence of a base such as sodium hydride, sodium ethoxide, excess triazole, or an alkali metal carbonate (e.g. potassium carbonate). The reaction temperature will depend upon the choice of reactants, solvents and base, but generally the reaction mixture is heated under reflux. The process generally consists of dissolving the reactants in a solvent and then isolating the product by removal of the reactant solvent in vacuo. Unreacted triazole can be removed by extraction of the product with a suitable solvent which is then washed with water. A crystallisation or other purification procedure may then be carried out if desired.

The α-halo ketones may be made by known methods.

The compound of general formula (II) may also be made by alkenylating, alkynylating or aralkylating a compound of general formula:

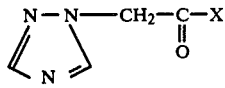

wherein X is as defined above. Further details of this reaction can be found in German Offenlegungsschrift No. 2610022, the disclosure of which document is incorporated herein by reference.

By way of example only the preparation of Compound No. 1 of Table I is hereinafter described in detail.

1-t-Butyl-2-(1,2,4-triazol-1-yl)-2-p-chlorobenzylethanol (Compound 1)

Stage I. 1,2,4-Triazole (33.4 g) and sodium ethoxide [from sodium (11.6 g) and ethanol (250 ml)] were refluxed for 1 hour. To this solution at the reflux temperature was added bromopinacolone (87 g), and heating was continued for a further 2 hours. The mixture was then cooled to ambient temperature, filtered to remove the precipitated sodium bromide and the solvent removed in vacuo. The residue was extracted with chloroform (100 ml). The solvent was washed with water (4×15 ml), dried (sodium sulphate) and filtered. Petroleum ether (50 ml; b.p. 60°–80°) was added and the solution concentrated to yield α-1,2,4-triazol-4-yl-pinacolone, m.p. 176°. Further concentration of the solution gave α-1,2,4-triazol-1-yl-pinacolone, m.p. 63°–65°.

Stage II. α-1,2,4-Triazol-1-yl-pinacolone (3.3 g) in dimethyl formamide (20 ml) was added dropwise to a suspension of sodium hydride (0.48 g; 100%) in dimethyl formamide (10 ml) at room temperature with stirring. After stirring for two hours, p-chlorobenzyl chloride (3.2 g) in dimethyl formamide (2–3 ml) was added dropwise and the reaction mixture was kept at 5°–10° for two hours. The solvent was removed in vacuo and water was added to the residue. The aqueous solution was extracted with methylene chloride, the organic layer was washed with water and dried (magnesium sulphate), and the solvent was removed. Crystallisation of the yellow solid gave α-p-chlorobenzyl-α-1,2,4-triazol-1-yl-pinacolone, m.p. 122°–123° as a white crystalline solid.

Stage III. A solution of the product (2.0 g) of Stage II in methanol (20 ml) was treated portionwise with sodium borohydride (0.26 g). The reaction mixture was then refluxed for one hour. The solvent was removed in vacuo and the hydrochloric acid (1 N; 40 ml) was added to the residue. The white precipitate was filtered off, washed with water, dried and crystallised from aqueous ethanol to give the title compound as a white crystalline solid, m.p. 162°–164°.

The antifungal substances Nos. 23 and 24 and others of this type may be made by reacting 1,2,4-triazole or a salt thereof with the appropriate α-halo ketone by any of the methods set out in the literature. Thus for example 1,2,4-triazole can be reacted with a α-halo ketone of general formula:

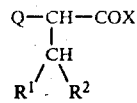

wherein Q is halogen (preferably bromine or chlorine) and X, R¹ and R² are as defined above.

This process may in some cases be carried out by merely heating the reactants together in the absence of a solvent or diluent, but preferably a solvent is present.

Suitable solvents are non-hydroxylic solvents such as acetonitrile (which is preferred), dimethylformamide, dimethyl sulphoxide, sulpholane and tetrahydrofuran. Hydroxylated solvents (e.g. methanol and ethanol) may be used in certain circumstances when the presence of the hydroxyl group does not interfere with the progress of the reaction.

The process may also be carried out in the presence of a base, but preferably excess triazole is present to remove liberated HX from the reaction. Other suitable bases include sodium hydride (although not when a hydroxylated solvent or diluent is used), alkali metal carbonates (such as potassium carbonate) and alkali metal hydroxides (such as potassium hydroxide). The temperature at which the reaction may be carried out will depend upon the choice of reactants, solvent and base, but generally the reaction mixture is heated under reflux.

The process generally involves dissolving the reactants in a solvent and, after allowing reaction to occur, isolating the product by removal of the reactant solvent in vacuo. Unreacted triazole is removed by extraction with a suitable solvent which is then washed with water. Crystallisation or other purification procedures may then be carried out, if desired.

The α-haloketone starting material may be made by any of the methods set out in the literature.

The compounds may also be made by aralkylating the corresponding compound of general formula (III):

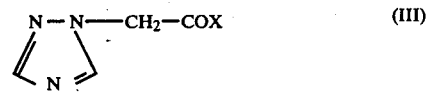

wherein X is as defined above, e.g. by first reacting it with an alkali metal hydride (e.g. sodium hydride) in a convenient solvent (such as dimethylformamide or tetrahydrofuran) to produce the alkali metal salt which is reacted with for example an α-alkylaralkyl halide e.g. a bromide (which is preferred) or a chloride.

This process generally involves dissolving the compound of general formula (III) in the solvent and adding an equivalent amount of the alkali metal hydride, and then, after allowing the reaction to occur, the α-alkylaralkyl halide is added dropwise. After the reaction, the product can be isolated by pouring into water and re-crystallising the solid formed from a convenient solvent, or purifying the resultant oil by column chromatography or another convenient technique.

The anti-fungal chemical substances used in the compositions and processes of the invention contain chiral centres. The compounds are generally obtained in the form of racemic mixtures or diastereoisomeric mixtures. However, these mixtures can be separated, if desired, into the individual isomers by methods known in the art. The scope of the invention is to be understood as including not only the racemic and diastereoisomeric mixtures, but also other mixtures of the isomers, and each of the individual isomers in isolation, as anti-fungal chemical substances useful for the compositions and processes of the invention.

Suitable salts are salts with inorganic or organic acids, for example hydrochloric, nitric, sulphuric, acetic and oxalic acids, of the anti-fungal chemical substances may be used in the invention compositions.

The metal complex is suitably one including copper, zinc, manganese or iron. It preferably has the general formula:

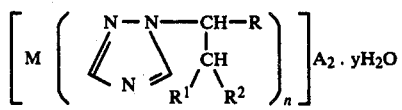

wherein R, R$_1$, and R$_2$ are as defined above, M is a metal, A is an anion (e.g. a chloride, bromide, iodide, nitrate, sulphate or phosphate anion), n is 2 or 4, and y is zero or an integer of 1 to 12.

The salts and metal complexes of the compounds of general formula (I) can be prepared in known manner. For example, the complexes can be made by reacting the uncomplexed compound with a metal salt in a suitable solvent.

The anti-fungal chemical substances used in the compositions and processes of this invention are active fungicides, particularly against the diseases: *Piricularia oryzae* on rice *Puccinia recondita, Puccinia striiformis* and other rusts on wheat, *Puccinia hordei, Puccinia striiformic* and other rusts on barley, and rusts on other hosts e.g. coffee, apples, vegetables and ornamental plants *Plasmopara viticola* on vines *Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines *Botrytis cinerea* (grey mould) on tomatoes, strawberries, vines and other hosts *Phytophthora infestans* (blight) on tomatoes *Venturia inaequalis* (scab) on apples *Rhynchosporium secalis*

The anti-fungal substances have also shown a broad range of activities against fungi in vitro. They are also active as seed dressings against: Fusarium spp. Septoria spp., Tilletia spp., Ustilago spp., Helminthosporium spp., and Pyrenophora spp. on cereals.

The anti-fungal chemical substances of the present invention have plant growth regulating activities.

The plant growth regulating effects of the substances are manifested as for example as stunting or dwarfing effect on the vegetative growth of mono- and dicotyledonous plants. Such stunting or dwarfing may be useful, for example, in cereals and soya bean where reduction in stem growth may reduce the risk of lodging. Substances which induce stunting or dwarfing may also be useful in stunting the growth of sugar in the cane at harvest. Stunting of peanuts can assist in harvesting. Growth retardation of grasses can help maintenance of grass swards.

Other plant growth regulating effects caused by the substances include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. The treatment of plants with the substances can lead to the leaves developing a darker green colour.

The foregoing plant growth regulating effects of the active anti-fungal chemical substances are controlled, as desired, for example compensated for (i.e. reduced or modified) to the desired extent by the use of the compositions of the present invention, or by the use of the plant or seed treatment processes of the invention.

The substances which may be used as constituent (b) of the invention compositions include the substances known as gibberellic acid and the gibberellins generally. These are well known in the plant-growth promotion art, and are widely documented and referenced. Some of these references are listed in the Merck Index (ninth edition) under the headings "Gibberellic Acid" and "Gibberellins" (see pp. 4250 and 4251 of the ninth edition). The structures of gibberellic acid (also known as Gibberellin A$_3$ or GA$_3$) and the other particularly useful, commercially available, gibberellins GA$_4$ and GA$_7$ (the latter are usually commercially available as a mixture) are, however, represented below. It is to be understood that the compositions of this invention may include a salt or derivative of gibberellic acid or other gibberellin. Mixtures of gibberellins are also embraced as constituents of the invention compositions.

Gibberellic Acid

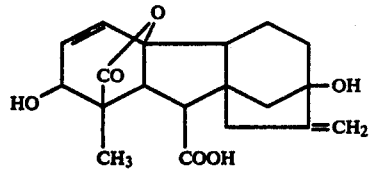

(U.K. Pat. No. 783611) (Gibberellic acid is also known as Gibberellin A$_3$ or GA$_3$).

Gibberellin A$_7$ (GA$_7$) (7-deoxy gibberellic acid)

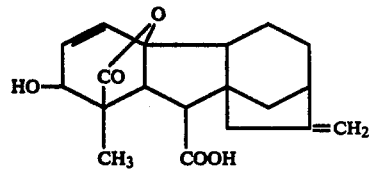

(British Pat. No. 914893)

Gibberellin A$_4$ (GA$_4$)

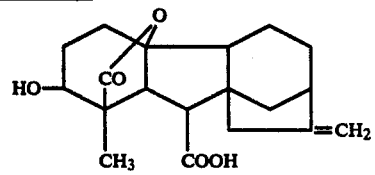

The invention compositions may contain varying proportions of the active fungicidal chemical and the gibberellic acid or other gibberellin, but a ratio, by weight, of from 1:5 to 1:50 of Gibberellic Acid or other Gibberellin to anti-fungal chemical is preferred. The preferred ratio is 1:5.

The invention compositions may contain, in addition to the usual adjuvants and fillers deployed in pesticidal compositions, in inorganic or organic acid to enhance the activity of the gibberellic acid or other gibberellin. Suitable acids are, for example, phosphoric acid and hydrochloric acid and various sulphonic-, hydroxy-, carboxylic- and dicarboxylic-acids. Citric acid and tartaric acids are preferred organic acids. The amount of acid by weight in the compositions may be up to ten times the amount of anti-fungal chemical substance.

The compositions may also contain alkali metal, alkaline earth metal, metal, or ammonium, salts to reduce the phytotoxicity or growth regulatory effects of the anti-fungal chemical substance and/or enhance the effect of the gibberellic acid or other gibberellin (or derivative or salt thereof). Zinc chloride and alkali metal, alkaline earth metal or ammonium salts of mineral acids, especially the nitrates, phosphates, sulphates, chlorides and carbonates of sodium, potassium, ammonium, magnesium and calcium are preferred.

The compositions of the invention may be in the form of dusting powders wherein the active substances are mixed with a solid diluent or carrier. Suitable diluents or carriers may be, for example, kaolin, bentonite, kieselguhr, dolomite, calcium carbonate, talc, powdered magnesia, Fuller's earth, gypsum, Hewitt's earth, diatomaceous earth and china clay. Compositions for dressing seed, for example, may comprise an agent assisting the adhesion of the composition to the seed, for example, a mineral oil.

The compositions may also be in the form of dispersible powders or grains comprising, in addition to the active substances, a wetting agent to facilitate the dispersion of the powder or grains in liquids. Such powders or grains may include fillers, suspending agents and the like.

The compositions may also be in the form of liquid preparations containing the active substances. Such liquid preparations for the invention process are generally solutions, aqueous dispersions or emulsions containing the active substances in the presence of one or more wetting (i.e. surface active) agents, dispersing agents, emulsifying agents or suspending agents. The amount, by weight of such surface active agents may be up to ten times the amount of anti-fungal chemical substance in any compositions according to the invention.

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene include, for example, the condensation products of ethylene oxide with fatty alcohols such as oleyl alcohol or cetyl alcohol, or with alkyl phenols such as octyl phenol, nonyl phenol and octyl cresol.

Other non-ionic agents are the partial esters derived from long chain fatty acids and hexitol anhydrides, the condensation products of the said partial esters with ethylene oxide, and the lecithins. Suitable suspending agents are, for example, hydrophilic colloids, for example, polyvinylpyrrolidone and sodium carboxymethylcellulose, and the vegetable gums, for example, gum acacia and gum tragacanth.

The aqueous solutions, dispersions or emulsions may be prepared by dissolving, dispersing or emulsifying the active substances in an organic solvent which may contain one or more wetting, dispersing or emulsifying agents. Suitable organic solvents are dimethyl formamide, ethylene dichloride, isopropyl alcohol, propylene glycol and other glycols, diacetone alcohol, toluene, kerosene, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane.

By the inclusion of suitable additives, for example, for improving the distribution, adhesive power and resistance to rain on treated surfaces, the different compositions can be better adapted for the various uses for which they are intended.

The compositions may also be conveniently formulated by admixing them with fertilisers. A preferred composition of this type comprises granules of fertiliser material incorporating an invention compound. The fertiliser material may, for example, comprise nitrogen, or phosphate-containing substances.

The compositions which are to be used in the form of aqueous dispersions or emulsions are generally supplied in the form of a concentrate containing a high proportion of the active substances, the said concentrate to be diluted with water before use.

The concentrates are often required to withstand storage for prolonged periods and after such storage, to be capable of dilution with water in order to form aqueous preparations which remain homogeneous for a sufficient time to enable them to be applied by conventional spray equipment.

The concentrates may conveniently contain up to 50% and generally from 10 to 20% by weight of the active substances.

When diluted to form aqueous preparations, such preparations may contain varying amounts of the active ingredient depending upon the purpose for which they are to be used, but an aqueous preparation containing between 0.002% and 0.2% by weight, and preferably 0.01 to 0.05% by weight of active ingredient may be used.

It is understood that the compositions of this invention may comprise, in addition to one or more active compounds according to the invention, one or more other substances having biological activity, for example, insecticidal, fungicidal, or bactericidal activity.

In certain aspects of this invention, and more particularly where the treatment, or dressing, of seed is concerned, it may be equally, or more, advantageous to apply the anti-fungal substance to the seed, either before, but preferably after, applying the gibberellic acid or other gibberellin. Simultaneous application to seed of both substances in the form of a composition according to the invention may also be used. A seed-dressing process, and apparatus therefore, may therefore be used in which, as consecutive steps, or simultaneously, the aforementioned substances are applied to the seed as a "dressing" or impregnation. Either one of, or both of, the substances may be admixed with a solid or liquid carrier substance for this purpose. Water or polar liquids of an organic character are preferred liquid carriers, especially dimethylformamide, N-methyl-2-pyrrolidone, tetrahydrofurfuryl alcohol, and glycols for their seed-penetrating ability. Non-aromatic hydrocarbons such as isoparaffins may be used, but, for example, lower-boiling dichloromethane and acetone may also be employed. Encapsulated formulations in which either, or both, substances are in the encapsulated form, may also be deployed.

In a further aspect, therefore, the invention provides a process for combating fungal diseases of plants and seeds (especially powdery mildews) which comprises treating the plants or seeds (especially cereals) with a composition as hereinbefore defined or with the constituents (a) and (b) of such a composition applied sequentially in any order.

The invention is illustrated, by way of example only, by the following examples, in which percentage amounts are on a weight basis. Examples 1, 2 and 3 illustrate compositions according to the invention and their use to combat fungal disease. Examples 4 to 16 illustrate compositions according to the invention.

EXAMPLE 1

Barley seeds of variety "Proctor" were germinated in soil drenched with a liquid preparation containing 250 or 500 parts per million (p.p.m.) of the fungicidal chemical substance No. 25 of Table I. At the same time the soil was treated with 1, 5 and 10 p.p.m. of gibberellic acid. The plants emerged three days after the seed was sown and after four more days their height was measured in millimeters.

The emergent plants were grown in a growth room where the day temperature was maintained at 75° (Fahrenheit scale) and the Relative Humidity at a value of 60%, and the night temperature at 67° (Fahrenheit Scale) and Relative Humidity at a value of 95%. The length of day was 16 hours.

The height figures measured and presented in the table below represent the mean value for 24 plants (3 replicate pots per treatment, with 8 plants grown in each pot) and the plant emergence recorded for the sown seed was substantially 100%.

dodecylbenzene at 2% as a sticker to assist adhesion to the seed).

Powdered formulations containing 10% and 25% of Gibberellin $A_3$ ($GA_3$) and a mixture of Gibberellin $A_4$ and Gibberellin $A_7$ ($GA_{4/7}$) were also prepared (these also contained talc and dodecylbenzene).

At the same time 50 gram amounts of wheat seed (variety Maris Butler) and barley seed (variety Proctor) were weighed into glass jars of 120 ml capacity to form individual batch amounts of seed.

To these jars (except those which were not treated at all or to which only fungicides Nos. 1 and 26 were added) were added the appropriate amounts by weight of the fungicide formulation and the gibberellin formulation ($GA_3$ or $GA_{4/7}$) so as to produce concentrations of 250 or 500 parts per million (p.p.m.) of the fungicidal chemical, and 10, 50 and 100 parts per million of the Gibberellin. The bottles were then shaken vigorously and then mechanically rotated for 20 minutes.

Two cubic centimeters of individual batches of seed were then shaken onto the surface of compost in 60 millimeter square plastic pots filled to 60 percent of their capacity with John Innes Potting Compost No. 1, the compost surface having been firmed and levelled. The seed was then covered with a layer of the same compost to a depth of 2 centimeters. The surface was again firmed by pressure. There were 3 replicates per treatment and per crop.

The pots were lightly watered from overhead and placed in a glasshouse at 16° C. Every 14 days they were fed with liquid fertiliser. The plants were inoculated 10 days after the sowing of the seed by shaking spore-infested plants over the grouped pots.

The disease for barley was *Erysiphe graminis* f. sp. hordei and the disease for wheat was *Erysiphe graminis* f. sp. tritici.

The heights of the emergent plants were measured in centimeters 11, 16 and 36 days after sowing. Average heights per pot replicate were calculated and the results of the experiment set out in the Tables below are the means of the three replicates.

Disease scores are on the gradings 0, 1, 2, 3, 4 where:
0 represents 61 to 100% disease present

TABLE II

| FUNGICIDAL CHEMICAL (SEE TABLE 1 FOR IDENTIFICATION LETTER | RATE OF APPLICATION IN P.P.M. OF FUNGICIDAL CHEMICAL | HEIGHT IN MILLIMETRES OF PLANTS PER RATE OF APPLICATION OF GIBBERELLIC ACID IN P.P.M. | | | |
|---|---|---|---|---|---|
| | | 10 | 5 | 1 | 0 |
| D | 500 | 65 | 62 | 47 | 50 |
| | 250 | 79 | 83 | 64.5 | 62.5 |
| GIBBERELLIC ACID (ALONE) | — | 144 | 150 | 124 | — |
| WATER (ALONE) | — | — | — | — | 129 |
| | — | — | — | — | 139 |
| ON GROWTH-ROOM SANDBED UNTREATED | — | — | — | — | 129 |

EXAMPLE 2

Compounds Nos. 1 and 26 of Table I were incorporated at 25% concentration into powdered seed dressing formulations (these contained talc as a filler and 1 represents 26 to 60% disease present
2 represents 6 to 25% disease present
3 represents 0 to 5% disease present
4 represents no disease present.

TABLE III

| | BARLEY SEEDLING PLANTS | | | | | | | |
|---|---|---|---|---|---|---|---|---|
| | COMPOUND NO 26 AT 250 P.P.M. | | | | COMPOUND NO 1 AT 250 P.P.M. | | | |
| CONCENTRATION OF | HEIGHT (CMS) AFTER DAYS | | | DISEASE | HEIGHT (CMS) AFTER DAYS | | | DISEASE |
| GA$_3$ (P.P.M.) | 11 | 16 | 36 | GRADING | 11 | 16 | 36 | GRADING |
| 10 | 5.6 | 8.3 | 10.6 | 4 | 4.9 | 7.5 | 6.3 | 4 |
| 50 | 6.8 | 10.5 | 12.6 | 4 | 6.3 | 9.5 | 10.0 | 4 |
| 100 | 8.2 | 11.7 | 14.6 | 4 | 7.0 | 12.5 | 12.0 | 4 |
| Fungicide only | 3.9 | 5.8 | 10.3 | 4 | 3.3 | 5.5 | 5.0 | 4 |
| Untreated | 9.3 | 13.5 | 24.3 | 1 | 9.3 | 13.5 | 24.3 | 1 |

TABLE IV

| | BARLEY SEEDLING PLANTS | | | | | | | |
|---|---|---|---|---|---|---|---|---|
| | COMPOUND NO 1 AT 500 P.P.M. | | | | GA$_3$ ALONE | | | |
| CONCENTRATION OF | HEIGHT (CMS) AFTER DAYS | | | DISEASE | HEIGHT (CMS) AFTER DAYS | | | DISEASE |
| GA$_3$ (P.P.M.) | 11 | 16 | 36 | GRADING | 11 | 16 | 36 | GRADING |
| 10 | 4.1 | 7.0 | 7.0 | 4 | 9.3 | 15.7 | 23 | 0 |
| 50 | 5.1 | 93 | 7.3 | 4 | 9.6 | 15.3 | 24.3 | 0 |
| 100 | 7.7 | 12.5 | 12.0 | 4 | 11.7 | 19.5 | 23 | 0 |
| Fungicide only | 3.1 | 4.8 | 4.3 | 4 | — | — | — | — |
| Untreated | 9.3 | 13.5 | 24.3 | 1 | 9.3 | 13.5 | 24.3 | 1 |

TABLE V

| | WHEAT SEEDLING PLANTS | | | | | | | |
|---|---|---|---|---|---|---|---|---|
| | COMPOUND NO 26 AT 250 P.P.M. | | | | COMPOUND NO 1 AT 250 P.P.M. | | | |
| CONCENTRATION OF | HEIGHT (CMS) AFTER DAYS | | | DISEASE | HEIGHT (CMS) AFTER DAYS | | | DISEASE |
| GA$_3$ (P.P.M.) | 11 | 16 | 36 | GRADING | 11 | 16 | 36 | GRADING |
| 10 | 3.7 | 7.5 | — | — | 3.1 | 9.0 | — | — |
| 50 | 4.9 | 9.7 | — | — | 4.9 | 13.0 | 13.83 | 4 |
| 100 | 5.5 | 11.3 | 13.66 | 4 | 5.7 | 15.6 | 18.66 | 4 |
| Fungicide only | 1.8 | 6.3 | 6.83 | 4 | 1.5 | 4.7 | 9.18 | 4 |
| Untreated | 7.7 | 16.5 | 27.33 | 0 | 7.7 | 16.5 | 27.33 | 0 |

TABLE VI

| | WHEAT SEEDLING PLANTS | | | | | | | |
|---|---|---|---|---|---|---|---|---|
| | COMPOUND NO 1 AT 500 P.P.M. | | | | GA$_3$ ALONE | | | |
| CONCENTRATION OF | HEIGHT (CMS) AFTER DAYS | | | DISEASE | HEIGHT (CMS) AFTER DAYS | | | DISEASE |
| GA$_3$ (P.P.M.) | 11 | 16 | 36 | GRADING | 11 | 16 | 36 | GRADING |
| 10 | 2.1 | 6.5 | — | — | 9.5 | 19.0 | 31.0 | 0 |
| 50 | 3.7 | 8.6 | — | — | 9.8 | 19.0 | 31.33 | 0 |
| 100 | 4.7 | 11.0 | 12.3 | 4 | 10.6 | 19.2 | 30.66 | 0 |
| Fungicide only | 1.1 | 3.5 | 5.6 | 4 | — | — | — | — |
| Untreated | 7.7 | 16.5 | 27.33 | 0 | 7.7 | 16.5 | 27.33 | 0 |

TABLE VII

| | BARLEY SEEDLING PLANTS | | | | | | | |
|---|---|---|---|---|---|---|---|---|
| | COMPOUND NO 26 AT 250 P.P.M. | | | | COMPOUND NO 1 AT 250 P.P.M. | | | |
| CONCENTRATION OF | HEIGHT (CMS) AFTER DAYS | | | DISEASE | HEIGHT (CMS) AFTER DAYS | | | DISEASE |
| GA$_{3/7}$ (P.P.M.) | 11 | 16 | 36 | GRADING | 11 | 16 | 36 | GRADING |
| 10 | 5.7 | 10 | 11 | 4 | 4.1 | 7.7 | — | — |
| 50 | 4.9 | 7.8 | 10.6 | 4 | 6.0 | 10.5 | 9.0 | 4 |
| 100 | 7.0 | 12.0 | 14.0 | 4 | 8.0 | 12.3 | 11.0 | 4 |
| Fungicide only | 3.9 | 5.8 | 10.3 | 4 | 3.3 | 5.5 | 5.0 | 4 |
| Untreated | 9.3 | 13.5 | 24.3 | 1 | 9.3 | 13.5 | 24.3 | 1 |

TABLE VIII

| | BARLEY SEEDLING PLANTS | | | | | | | |
|---|---|---|---|---|---|---|---|---|
| | COMPOUND NO 1 AT 500 P.P.M. | | | | GA$_{4/7}$ ALONE | | | |
| CONCENTRATION OF | HEIGHT (CMS) AFTER DAYS | | | DISEASE | HEIGHT (CMS) AFTER DAYS | | | DISEASE |
| GA$_{4/7}$ (P.P.M.) | 11 | 16 | 36 | GRADING | 11 | 16 | 36 | GRADING |
| 10 | 3.7 | 6.3 | — | — | 8.6 | 14.5 | 22.3 | 1 |
| 50 | 5.8 | 9.2 | 7 | 4 | 9.3 | 15.8 | 23.3 | 1 |
| 100 | 6.0 | 9.8 | 9 | 4 | 11.5 | 16.5 | 22.3 | 1 |
| Fungicide Only | 3.1 | 4.8 | 4.3 | 4 | — | — | — | — |
| Untreated | 9.3 | 13.5 | 24.3 | 1 | 9.3 | 13.5 | 24.3 | 1 |

TABLE IX

| | WHEAT SEEDLING PLANTS | | | | | | | |
|---|---|---|---|---|---|---|---|---|
| | COMPOUND NO 26 AT 250 P.P.M. | | | | COMPOUND NO 1 AT 250 P.P.M. | | | |
| CONCENTRATION OF | HEIGHT (CMS) AFTER DAYS | | | DISEASE | HEIGHT (CMS) AFTER DAYS | | | DISEASE |
| GA$_{4/7}$ (P.P.M.) | 11 | 16 | 36 | GRADING | 11 | 16 | 36 | GRADING |
| 10 | 3.6 | 8.8 | — | — | 5.1 | 11.2 | 12.0 | 4 |
| 50 | 4.1 | 9.0 | 12.33 | 4 | 7.1 | 13.8 | 17.33 | 4 |
| 100 | 4.6 | 12.5 | 14.66 | 4 | 7.8 | 15.3 | 17.0 | 4 |
| Fungicide only | 1.8 | 6.3 | 6.83 | 4 | 1.5 | 4.7 | 9.18 | 4 |
| Untreated | 7.7 | 16.5 | 27.33 | 0 | 7.7 | 16.5 | 27.33 | 0 |

TABLE X

| | WHEAT SEEDLING PLANTS | | | | | | | |
|---|---|---|---|---|---|---|---|---|
| | COMPOUND NO 1 AT 500 P.P.M. | | | | GA$_{4/7}$ ALONE | | | |
| CONCENTRATION OF | HEIGHT (CMS) AFTER DAYS | | | DISEASE | HEIGHT (CMS) AFTER DAYS | | | DISEASE |
| GA$_{4/7}$ (P.P.M.) | 11 | 16 | 36 | GRADING | 11 | 16 | 36 | GRADING |
| 10 | 3.9 | 8.6 | — | — | 8.6 | 17.0 | 30.66 | 0 |
| 50 | 4.6 | 11.2 | 13.5 | 4 | 9.4 | 18.7 | 31.0 | 0 |
| 100 | 5.8 | 11.3 | 13.83 | 4 | 9.8 | 18.7 | 31.0 | 0 |
| Fungicide only | 1.1 | 3.5 | 5.6 | 4 | — | — | — | — |
| Untreated | 7.7 | 16.5 | 27.33 | 0 | 7.7 | 16.5 | 27.33 | 0 |

EXAMPLE 3

A. In this experiment various formulations of the fungicidal chemicals of Table I were made up and applied at the rates of active chemical of 250, 100 and 50 parts per million to wheat seeds (variety Maris Butler) and to barley seeds (variety Midas). In each case the seed was confirmed previously to have a 90% germinability.

The precise nature of the treatments is set out in the following Table.

TABLE XI

| TREATMENT NO | RATE OF APPLICATION WITH RESPECT TO FUNGICIDAL CHEMICAL | COMPONENTS OF FORMULATION |
|---|---|---|
| 1 | 250 | Compound No 1 (10%) - of Table I |
| 2 | 100 | GA$_3$ (2%) |
| 3 | 50 | Dodecylbenzene |
| | | Talc |
| 4 | 250 | As for treatments 1 to 3 but plus |
| 5 | 100 | Citric Acid (40%) |
| 6 | 50 | |
| 7 | 250 | As for treatments 1 to 3 but plus |
| 8 | 100 | Tartaric Acid (40%) |
| 9 | 50 | |
| 10 | 250 | As for treatments 1 to 3 but plus |
| 11 | 100 | EDTA disodium salt |
| 12 | 50 | (Note EDTA = Ethylenediamine-tetracetic acid) |
| 13 | 250 | As for treatments 1 to 3 but plus |
| 14 | 100 | Succinic Acid (40%) |
| 15 | 50 | |
| 16 | 250 | As for treatments 1 to 3 but plus |
| 17 | 100 | filler and plus Cirrasol ALNWF |
| 18 | 50 | (2%) |
| 19 | 250 | As for treatments 1 to 3 but plus |
| 20 | 100 | filler and plus Cirrasol ALNWF |
| 21 | 50 | (4%) |
| 22 | 250 | As for treatments 1 to 3 but plus |
| 23 | 100 | filler and plus Cirrasol ALNWF |
| 24 | 50 | (10%) |
| 25 | 250 | Compound No 1 (20%) of Table I |
| 26 | 100 | GA$_3$ (4%) |
| 27 | 50 | Triton X100 (2%) |
| | | Propylene glycol |
| 28 | 250 | Compound No 11 (20%) of Table I |
| 29 | 100 | GA$_3$ (4%) |
| 30 | 50 | Dimethyl formamide |
| 31 | 250 | Compound No 11 (20%) of Table I |
| 32 | 100 | GA$_3$ (4%) |
| 33 | 50 | Triton X100 (2%) |
| | | Propylene Glycol |
| 34 | 250 | Compound No 1 of Table I as para-toluene sulphonate salt |
| 35 | 100 | Dodecylbenzene |
| 36 | 50 | Talc |
| 37 | — | Untreated Control Plants disease infected by bulk inoculation |
| 38 | | Untreated Control Plants naturally |

TABLE XI-continued

| TREAT-MENT NO | RATE OF APPLICATION WITH RESPECT TO FUNGICIDAL CHEMICAL | COMPONENTS OF FORMULATION |
|---|---|---|
| | | infected* |

(*i.e. Plants in greenhouse exposed to ambient mildew)

Each formulation was applied to 50 g samples of clean seed at three rates giving 250, 100 and 50 p.p.m. of fungicide respectively. This was achieved by weighing the appropriate amount of formulation and adding it to 50 g of seed in an 8 oz jar followed by immediate rapid shaking for 1 minute, and then 20 minutes on a mechanical rotator.

12 Seeds were sown, evenly spaced, in each of 3 replicate 14 cm diameter pots per treatment. The pots were kept in a glasshouse at 15°–20° C. and watered from above. Emergence counts were done at 7 days after sowing. The height of prophylls of all seedlings was determined 12 days after sowing. The pots were randomised on the bench after the prophylls were fully developed.

The barley plants were bulk inoculated by shaking a spore infested plant over the grouped pots 16 days after sowing at a time when the controls had prophyll plus 2 fully extended leaves). Plant height was measured 18 days after sowing.

The wheat plants were bulk inoculated 18 days after sowing (control plants had prophyll plus 2 fully extended leaves). Heights were assessed 20 days after sowing.

The diseases used for the barely and the wheat were the same as those deployed in Example 2.

Mildew was assessed on wheat plants by sampling leaf blades from the third leaf down from the youngest leaf showing at growth stage 7*. Ten such leaf blades were sampled per treatment and the percentage cover of the adaxial surface by mildew recorded.
* on the Feekes scale Not much activity growing and sporing mildew appeared on the barley despite bulk inoculation on two occasions and continuous exposure to embient mildew in the glasshouse. However mildew attack was assessable after 5 weeks (see Results Section for details).

TABLE XII

| WHEAT SEEDLING PLANTS - EMERGENCE | | | |
|---|---|---|---|
| TREATMENT NO | PERCENTAGE EMERGENCE | TREATMENT NO | PERCENTAGE EMERGENCE |
| 1 | 38.0 | 13 | 44.1 |
| 2 | 67.4 | 14 | 40.5 |
| 3 | 66.8 | 15 | 61.4 |
| 4 | 69.5 | 16 | 47.1 |
| 5 | 78.2 | 17 | 46.6 |
| 6 | 66.8 | 18 | 49.4 |
| 7 | 72.8 | 19 | 59.0 |
| 8 | 73.4 | 20 | 67.1 |
| 9 | 66.8 | 21 | 53.7 |
| 10 | 43.8 | 22 | 47.1 |
| 11 | 73.4 | 23 | 86.4 |
| 12 | 64.1 | 24 | 83.9 |
| 25 | 80.7 | 32 | 66.8 |
| 26 | 92.3 | 33 | 76.5 |
| 27 | 69.7 | 34 | 41.7 |
| 28 | 67.5 | 35 | 46.9 |
| 29 | 72.6 | 36 | 36.5 |
| 30 | 77.0 | 37 | 94.5 |
| 31 | 58.7 | 38 | 99.1 |

BARLEY SEEDLING PLANTS-EMERGENCE

None of the treatments 1 to 36 significantly reduced emergence.

TABLE XIII

| WHEAT AND BARLEY SEEDLING PLANTS | | | | |
|---|---|---|---|---|
| TREATMENT NO | HEIGHT (mms) AFTER 7 DAYS | | HEIGHT (mms) AFTER 12 DAYS | |
| | WHEAT | BARLEY | WHEAT | BARLEY |
| 1 | 12.4 | 19.6 | 43.7 | 76.9 |
| 2 | 10.8 | 15.3 | 53.8 | 72.9 |
| 3 | 11.2 | 16.9 | 56.4 | 74.6 |
| 4 | 9.3 | 14.9 | 52.7 | 72.6 |
| 5 | 10.2 | 16.5 | 58.6 | 72.7 |
| 6 | 11.5 | 14.9 | 54.7 | 71.7 |
| 7 | 12.0 | 18.5 | 59.6 | 80.5 |
| 8 | 12.4 | 17.6 | 58.2 | 75.3 |
| 9 | 11.5 | 15.2 | 54.9 | 76.1 |
| 10 | 9.5 | 17.4 | 45.5 | 76.4 |
| 11 | 9.9 | 17.2 | 54.0 | 76.8 |
| 12 | 10.5 | 12.1 | 53.2 | 66.4 |
| 13 | 9.6 | 16.5 | 49.7 | 75.0 |
| 14 | 8.7 | 14.2 | 50.1 | 68.0 |
| 15 | 11.5 | 16.2 | 54.1 | 72.8 |
| 16 | 9.1 | 16.9 | 49.6 | 70.2 |
| 17 | 9.6 | 18.2 | 46.4 | 76.7 |
| 18 | 9.9 | 13.8 | 44.8 | 71.1 |
| 19 | 11.0 | 12.2 | 51.5 | 63.1 |
| 20 | 12.4 | 13.5 | 59.7 | 64.7 |
| 21 | 11.2 | 18.4 | 51.3 | 77.9 |
| 22 | 11.6 | 20.1 | 50.5 | 72.8 |
| 23 | 13.2 | 20.1 | 56.6 | 75.2 |
| 24 | 11.4 | 20.4 | 60.6 | 80.2 |
| 25 | 13.4 | 17.5 | 60.6 | 77.4 |
| 26 | 10.7 | 15.2 | 56.8 | 72.2 |
| 27 | 13.5 | 11.8 | 54.5 | 71.3 |
| 28 | 11.8 | 13.1 | 59.4 | 78.3 |
| 29 | 14.1 | 17.2 | 64.3 | 80.9 |
| 30 | 12.2 | 13.4 | 64.0 | 76.9 |
| 31 | 10.3 | 19.3 | 52.2 | 84.5 |
| 32 | 10.4 | 14.6 | 55.3 | 76.9 |
| 33 | 12.4 | 16.6 | 60.8 | 79.4 |
| 34 | 4.9 | 6.4 | 31.9 | 42.7 |
| 35 | 5.4 | 7.7 | 36.6 | 50.3 |
| 36 | 8.2 | 9.4 | 42.5 | 53.7 |
| 37 | 18.6 | 16.5 | 78.6 | 80.6 |
| 38 | 18.0 | 18.6 | 73.4 | 80.6 |

TABLE XIV

| WHEAT SEEDLING PLANTS MEAN PERCENTAGE COVER BY MILDEW OF UPPER SURFACE OF THIRD EXPOSED LEAF (FROM TOP OF PLANT) (MEAN OF 10 BLADES PER TREATMENT) | | | |
|---|---|---|---|
| TREATMENT NO | PERCENTAGE MILDEW COVER | TREATMENT NO | PERCENTAGE MILDEW COVER |
| 1 | 35 | 9 | 82 |
| 2 | 38 | 10 | 6 |
| 3 | 58 | 11 | 59 |
| 4 | 18 | 12 | 78 |
| 5 | 50 | 13 | 42 |
| 6 | 72 | 14 | 51 |
| 7 | 9 | 15 | 100 |
| 8 | 40 | 16 | 44 |
| 17 | 56 | 28 | 5 |
| 18 | 98 | 29 | 10 |
| 19 | 28 | 30 | 22 |
| 20 | 60 | 31 | 68 |

TABLE XIV-continued

WHEAT SEEDLING PLANTS
MEAN PERCENTAGE COVER BY MILDEW OF
UPPER SURFACE OF THIRD EXPOSED LEAF
(FROM TOP OF PLANT)
(MEAN OF 10 BLADES PER TREATMENT)

| TREATMENT NO | PERCENTAGE MILDEW COVER | TREATMENT NO | PERCENTAGE MILDEW COVER |
|---|---|---|---|
| 21 | 67 | 32 | 86 |
| 22 | 47 | 33 | 94 |
| 23 | 78 | 34 | 67 |
| 24 | 100 | 35 | 100 |
| 25 | 28 | 36 | 100 |
| 26 | 68 | 37 | 100 |
| 27 | 100 | 38 | 0 |

TABLE XV

BARLEY SEEDLING PLANTS
(VARIETY MIDAS)
Mean Number of hypersensitive
lesions caused by Mildew on 10 centimeter
length of leaf blade of third leaf from apex.

| TREATMENT NO. | NO. LESIONS | TREATMENT NO. | NO. LESIONS |
|---|---|---|---|
| 1 | 28 | 11 | 35 |
| 2 | 59 | 12 | 40 |
| 3 | 63 | 13 | 10 |
| 4 | 29 | 14 | 44 |
| 5 | 63 | 15 | 33 |
| 6 | 79 | 16 | 24 |
| 7 | 20 | 17 | 65 |
| 8 | 35 | 18 | 48 |
| 9 | 50 | 19 | 19 |
| 10 | 12 | 20 | 67 |
| 21 | 60 | 30 | 53 |
| 22 | 44 | 31 | 21 |
| 23 | 73 | 32 | 55 |
| 24 | 99 | 33 | 78 |
| 25 | 14 | 34 | 9 |
| 26 | 46 | 35 | 30 |
| 27 | 95 | 36 | 58 |
| 28 | 41 | 37 | 80 |
| 29 | 83 | (infected control) | |

B. In a further experiment using barley seed of a different, and more mildew-susceptible, variety (variety Proctor) the treatment 1 to 36 set out in A above were all repeated, and further treatments 37 to 46 used in addition. These were as follows:

TABLE XVI

| TREATMENT NO | RATE OF APPLICATION OF ANTI-FUNGAL | COMPONENTS OF FORMULATION |
|---|---|---|
| 37 | 250 | Compound No 1 of Table I (40%) |
| 38 | 100 | Gibberellin A$_3$ (4%) |
| 39 | 50 | Dimethylformamide (56%) |
| 40 | 250 | Gibberellin A$_3$ (2%) |
| 41 | 100 | Dimethylformamide (98%) |
| 42 | 50 | |
| 43 | — | Untreated - Bulk Inoculated |
| 44 | 250 | Compound No 1 of Table I (25%) |
| 45 | 100 | Talc (75%) |
| 46 | 50 | |

The procedure for treating and sowing the seed was exactly as described in experiment A. above.

Twelve days after sowing the only treatments which produced stunted seedling plants were Nos. 34 to 36 and 44 to 46. Since these were the only treatments in which Gibberellin A$_3$ was absent it was clear that the latter was reversing the stunting effects of the anti-fungal chemical substances used in the other treatments.

The plants were then bulk inoculated (in the manner described under A) with spores of the same disease for barley. The prophylls were assesed for mildew 7 days, 14 days and 28 days later.

The results are presented in the Table below:

TABLE XVII

BARLEY SEEDLING PLANTS (VARIETY PROCTOR)
MEAN NUMBER OF MILDEW COLONIES ON PROPHYLLS

| TREATMENT NO | ASSESSMENT AFTER DAYS | | |
|---|---|---|---|
| | 7 | 14 | 28 |
| 1 | 0 | 25 | 15 |
| 2 | 0 | 36 | 39 |
| 3 | 22 | 90 | 62 |
| 4 | 0 | 12 | 18 |
| 5 | 6 | 102 | 41 |
| 6 | 38 | 255 | 43 |
| 7 | 0 | 25 | 10 |
| 8 | 4 | 72 | 46 |
| 9 | 26 | 194 | 36 |
| 10 | 0 | 8 | 16 |
| 11 | 1 | 83 | 62 |
| 12 | 33 | 197 | 54 |
| 13 | 0 | 5 | 6 |
| 14 | 0 | 34 | 36 |
| 15 | 10 | 157 | 53 |
| 16 | 0 | 5 | 2 |
| 17 | 0 | 83 | 58 |
| 18 | 22 | 163 | 48 |
| 19 | 0 | 4 | 11 |
| 20 | 4 | 81 | 50 |
| 21 | 16 | 125 | 68 |
| 22 | 0 | 3 | 1 |
| 23 | 18 | 168 | 22 |
| 24 | 6 | 100 | 31 |
| 25 | 0 | 6 | 12 |
| 26 | 3 | 75 | 47 |
| 27 | 20 | 156 | 40 |
| 28 | 12 | 62 | 10 |
| 29 | 71 | 200 | 51 |
| 30 | 104 | 260 | 32 |
| 31 | 0 | 98 | 26 |
| 32 | 3 | 166 | 31 |
| 33 | 53 | 226 | 33 |
| 34 | 39 | 192 | 22 |
| 35 | 100 | 304 | 47 |
| 36 | 153 | 454 | 65 |
| 37 | 0 | 17 | 13 |
| 38 | 49 | 212 | 45 |
| 39 | 4 | 167 | 40 |
| 40 | 113 | 617 | 140 |
| 41 | 103 | 715 | 88 |
| 42 | 161 | 684 | 144 |
| 43 | 193 | 363 | 72 |
| 44 | — | 5 | 2 |
| 45 | — | 25 | 10 |
| 46 | — | 65 | 30 |

The foregoing experiments demonstrate the effectiveness of the compositions of the invention in controlling fungal disease and protecting plants from severe attack whilst reducing the degree of stunting caused by the specific fungicidally-active chemicals they contain. The results also demonstrate that the enhancement of the effects of the gibberellin by the incorporation of acids is, surprisingly, unaffected or undiminished by the presence of the fungicidal chemicals, and the other formulation adjuvants. The advantages of incorporating "Cirrasol" ALNWF surface active agent in the invention compositions is also readily apparent.

EXAMPLE 4

This example illustrates a dusting powder which may be applied directly to plants or other surfaces and comprises 5% by weight of Compound No. 1 of Table I, 1% by weight of gibberellic acid and 94% by weight of talc.

EXAMPLE 5

The ingredients listed below were ground together in the proportions stated to produce a powdered mixture readily dispersible in liquid.

|  | % wt. |
|---|---|
| Compound No. 1 of Table I | 45 |
| Gibberellic acid | 5 |
| 'Dispersol' T ('Dispersol' is a Trade Mark) | 5 |
| China clay | 45 |
|  | 100% |

EXAMPLE 6

A composition in the form of grains readily dispersible in a liquid (for example water) was prepared by grinding together the first four of the ingredients listed below in the presence of water and then the sodium acetate was mixed in. The admixture was dried and passed through a British Standard mesh sieve, size 44–100 to obtain the desired size of grains.

|  | % wt. |
|---|---|
| Compound No. 1 of Table I | 48 |
| Gibberellic Acid | 2 |
| 'Dispersol' T | 12.5 |
| Calcium lignosulphonate | 5 |
| Sodium dodecylbenzenesulphonate | 12.5 |
| Sodium acetate | 20 |
|  | 100% |

EXAMPLE 7

A composition suitable for use as a seed dressing was prepared by mixing all three of the ingredients set out below in the proportions stated.

|  | % wt. |
|---|---|
| Compound No. 1 of Table I | 75 |
| Gibberellic Acid | 5 |
| Mineral oil | 2 |
| China clay | 18 |
|  | 100% |

EXAMPLE 9

The following constituents were admixed to form a powdered seed dressing formulation.

| Compound No. 1 of Table I | 20% |
|---|---|
| Gibberellin $A_3$ ($GA_3$) | 4% |
| Talc | 76% |

EXAMPLE 10

The substances listed below were mixed in the stated proportions to produce a liquid seed dressing formulation.

| Compound No. 1 of Table I | 20% |
|---|---|
| Gibberellin $A_3$ ($GA_3$) | 4% |
| Dimethylformamide | 100% |

EXAMPLE 11

The following substances were mixed to form a powdered seed dressing composition.

| Compound No. 1 of Table I | 10% |
|---|---|
| Gibberellin $A_3$ ($GA_3$) | 2% |
| Tartaric acid | 40% |
| Filler (Talc) | 48% |

EXAMPLE 12

The following substances were mixed together in the proportions stated to produce a liquid composition suitable for use as a seed dressing.

| Compound No. 1 of Table I | 10% |
|---|---|
| Gibberellin $A_3$ ($GA_3$) | 2% |
| Tartaric acid | 20% |
| Dimethylformamide | 48% |

EXAMPLE 13

The following composition ingredients were thoroughly mixed together in the recited proportions to produce a powdered (a), and a liquid (b), formulation.

| (a) | |
|---|---|
| Compound No. 1 of Table I | 10% |
| $GA_3$ | 2% |
| "Cirrasol" ALN-WF | 10% |
| Talc filler | 78% |
| (b) | |
| Compound No. 1 of Table I | 20% |
| $GA_3$ | 1% |
| "Cirrasol" ALN-WF | 20% |
| Dimethylformamide | 59% |

EXAMPLE 14

The following constituent substances were mixed together, to form a liquid formulation, in the proportion stated.

| Compound No. 1 of Table I | 20% |
|---|---|
| Zinc chloride | 10% |
| $GA_3$ | 4% |
| Dimethylformamide | 66% |

EXAMPLE 15

A powdered formulation was prepared by mixing together the following substances in the amounts given.

| Compound No. 1 of Table I | 20% |
|---|---|
| Zinc chloride | 10% |
| $GA_3$ | 4% |
| Talc (filler) | 66% |

The following constitutes an explanation of the compositions or substances represented by the various Trade Marks and Trade Names referred to in the foregoing Examples.

| | |
|---|---|
| "DISPERSOL" T | is a mixture of sodium sulphate and a condensate of formaldehyde with the sodium salt of naphthalene sulphonic acid. |
| "CIRRASOL" ALN-WX | is a non-ionic surface-active agent which is a condensate of one mole of a long chain ($C_{16}$ to $C_{18}$) aliphatic alcohol with 17 moles of ethylene oxide. |
| "TRITON" X100 | is a surface-active agent which is the iso-octyl phenyl ether of polyethylene glycol. |

What is claimed is:

1. A process for combating powdery mildew in cereal seed which comprises treating said seed with an effective amount of a synergistic combination of gibberellic acid and a compound of the formula:

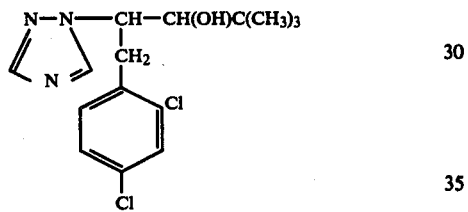

, the ratio of said compound of gibberellic acid being 50:1 to 5:1.

2. A process for combating powdery mildew in cereal seed which comprises treating said seed with an effective amount of a synergistic combination of gibberellic acid and a compound of the formula:

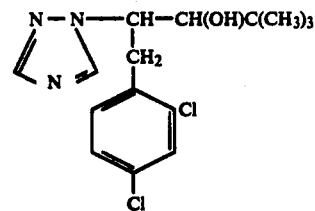

[or]

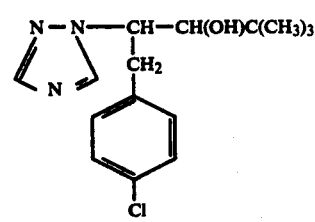

[or]

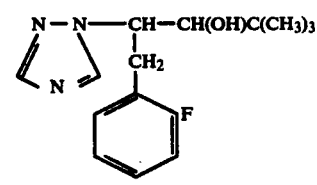

or

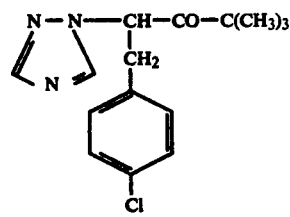

, the ratio of said compound to gibberellic acid being 50:1 to 5:1.

* * * * *